US005650278A

United States Patent [19]
Barr et al.

[11] Patent Number: 5,650,278
[45] Date of Patent: Jul. 22, 1997

[54] COMPOSITIONS AND DIAGNOSTIC KITS FOR IDENTIFYING ALVEOLAR RHABDOMYOSARCOMA

[75] Inventors: Frederic G. Barr, Philadelphia; Beverly S. Emanuel, Broomall; Naomi Galili, Wayne, all of Pa.

[73] Assignees: Children's Hospital of Philadelphia; Trustees of The University of Pennsylvania; The Wistar Institute of Anatomy and Biology, all of Philadelphia, Pa.

[21] Appl. No.: 329,055

[22] Filed: Oct. 25, 1994

Related U.S. Application Data

[63] Continuation of Ser. No. 26,896, Mar. 5, 1993, abandoned, which is a continuation of Ser. No. 995,084, Dec. 22, 1992, abandoned.

[51] Int. Cl.$^6$ ........................................................ C12Q 1/68
[52] U.S. Cl. .......................... 435/6; 536/24.31; 536/24.33
[58] Field of Search ............................. 435/6; 536/24.31; 531/24.33

[56] References Cited

U.S. PATENT DOCUMENTS

| | | | |
|---|---|---|---|
| 4,736,866 | 4/1988 | Leder et al. | 800/1 |
| 4,873,191 | 10/1989 | Wagner et al. | 435/172.3 |

OTHER PUBLICATIONS

Shapiro et al., Genes, Chromosomes & Cancer, 4:241–9, 1992.
1988 Stratagene Catalog, p. 39.
Douglass, E.C. et al., *A Specific Chromosomal Abnormality In Rhabdomyosarcoma*, (1987), Cytogenetics and Cell Genetics 45:148–155.
Crescenzi, M. et al., *Thermostable DNA Polymerase Chain Amplification of t (14;18) Chromosome Breakpoints and Detection of Minimal Residual Disease*, (Jul. 1988), Proc. Nat'l. Acad. Sci. USA 85:4869–4873.
Lee, M. et al., *Detection of Minimal Residual ber/abl Transcripts by a Modified Polymerase Chain Reaction*, (1988), Blood 72 (3):893–897.
Sawyers, C.L. et al. *Molecular Replase in Chronic Myelogenous Leukemia Patients After Bone Marrow Transplantation Detected By Polymerase Chain Reaction*, (1990), Proc. Natl. Acad. Sci. USA 87:563–567.
Kawasaki, E.S. et al., *Diagnosis of Chronic Myeloid and Acute Lymphocytic Leukemias by Detection of Leukemia-Specific mRNA Sequences Amplified in Vitro*, (1988), Proc. Natl. Acad. Sci. USA 85:5698–5702.
Barr, F.G., et al., *Localization of the Rhabdomyosarcoma t (2;13) Breakpoint on a Physical Map of Chromosome 13*, (1991) Genomics 11:941.
Barr, F.G. et al., *Localization of the t(2;13) Breakpoint of Alveolar Rhabdomyosarcoma on a Physical Map of Chromosome 2*, (1992) Genomics 13:1150.
Burrie, M., et al., *Conservation of the Paired Domain in Metazzoans and its Structure in Three Isolated Human Genes*, (1989) Embo J. 8:1183.
Goulding, M.D. et al., *Pax–3, a novel murine DNA Binding Protein Expressed During Early Neurogenesis*, (1991) Cell 67:767.
Epstein, D.J. et al., *Splotch (Sp2H), a Mutation Affecting Development of the Mouse Neural Tube, Shows a Deletion within the Paired Homeodomain of PAX–3*, (1991) Cell 67:767.
Cleary, M.L., *Oncogenic Conversion of Transcription Factors by Chromosomal Translocations*, (1991), Cell 66:619.
Lee, M. et al., *Detection of Minimal Residual Cells Carrying the t(14;18) by DNA Sequence Amplification*, (1987) Science 237:175–178.
Rabbits, T.H., *Translocations, Master Genes, and Differences between the Origins of Acute and Chronic Leukemias*, (1991) Cell 67:641.

*Primary Examiner*—Scott W. Houtteman
*Attorney, Agent, or Firm*—Woodcock Washburn Kurtz Mackiewicz & Norris

[57] ABSTRACT

Methods of determining whether a tumor is an alveolar rhabdomyosarcoma tumor by detecting the presence of a DNA sequence of a chimeric gene that is generated by translocation of a portion of human chromosome 2 and a portion of human chromosome 13 are disclosed. In addition, diagnostic kits to practice methods of determining whether a tumor is an alveolar rhabdomyosarcoma tumor are disclosed. Isolated nucleic acid molecules which comprise nucleotide sequences that are complementary to at least a portion of human chromosome 2 or a portion of human chromosome 13 are disclosed.

17 Claims, 6 Drawing Sheets

COMPOSITIONS AND DIAGNOSTIC KITS FOR IDENTIFYING ALVEOLAR RHABDOMYOSARCOMA

CROSS REFERENCE TO RELATED APPLICATIONS

This application is a continuation of U.S. patent Ser. No. 08/026,896, filed Mar. 5, 1993, now abandoned which is a continuation of U.S patent application Ser. No. 07/995,084 filed Dec. 22, 1992, now abandoned.

FIELD OF THE INVENTION

The present invention relates to nucleic acid sequence-based methods of identifying alveolar rhabdomyosarcoma and to diagnostic kits for performing such methods.

BACKGROUND OF THE INVENTION

Alveolar rhabdomyosarcoma is a soft tissue tumor which occurs in the pediatric population. Because of its aggressive behavior and associated poor prognosis, it is clinically important to distinguish this tumor from the embryonal subtype of rhabdomyosarcoma as well as other pediatric neoplasms. However, histologic diagnosis is often complicated by the paucity of features of striated muscle differentiation and its similarity to a large group of pediatric solid tumors that can present as collections of poorly differentiated small, round cells.

The course of action to be taken in a patient exhibiting small, round cell tumors is difficult to select because each tumor type in this category has its own treatment regimen. Patients suffering from alveolar rhabdomyosarcoma must be treated with surgery and a relatively potent and specific chemotherapy regimen. Because the determination of whether a tumor is alveolar rhabdomyosarcoma or not suggests the prognosis and what course of treatment is warranted, it is crucial to be able to identify whether or not a tumor is alveolar rhabdomyosarcoma in a fast, efficient and reliable manner.

If a tumor is diagnosed as being alveolar rhabdomyosarcoma, aggressive treatment for patients suffering from such tumors is undertaken to destroy and/or remove it.

After surgery is performed, there is a need to determine whether or not the surgeon removing the tumor has removed a sufficiently large section of tissue to ensure that no malignant cells remain. Normally, tissue from the margin of surgical resection is obtained and analyzed by a pathologist who examines the material to detect alveolar rhabdomyosarcoma cells. There are shortcomings to these procedures; in particular, it is very possible that tumor cells which are present can escape detection.

In addition to examining surrounding tissue to determine if metastasis has taken place, it is also desirable to test bone marrow. Using the currently available techniques, such examinations are insufficiently sensitive in many cases.

Moreover, early detection of reoccurring tumors is desirable in order to indicate the need to begin therapy again. It is desirable to be able to detect cells at the earliest possible time.

Cytogenetic investigations have recently identified a characteristic translocation of chromosome 2 and 13 t(2;13) (q35;q14) in the majority of alveolar rhabdomyosarcomas (Douglass, E. C. et al., (1987) *Cytogenetics and Cell Genetics* 45:148–155). That is, a portion of chromosome 2 and a port of chromosome 13 each break off from their respective chromosomes and attach to the other chromosome. Thus, in the alveolar rhabdomyosarcoma cells, the derivative chromosome 2 contains a portion of chromosome 13 and the derivative chromosome 13 contains a portion of chromosome 2.

The association of alveolar rhabdomyosarcoma with a specific chromosomal translocation permits alveolar rhabdomyosarcoma cells to be distinguished from other small, round tumor cells by microscopic examination of genetic material from tumor cells. Metaphase chromosomes must be observed and abnormalities detected. Karyotypes are made using the chromosomes from tumor cells. Chromosomes 2 and 13 are visually inspected to discover whether or not translocation has occurred. This procedure has several shortcomings. It is time consuming and relies on unpredictable growth and chromosomal banding characteristics of the tumor cells. Moreover, it requires a high degree of expertise and often repeated attempts.

Accordingly, there is a need for an improved method of detecting the presence of alveolar rhabdomyosarcoma tumor cells.

SUMMARY OF THE INVENTION

The molecular nature of the translocation has been elucidated and the present invention provides a fast, efficient and reliable means to distinguish alveolar rhabdomyosarcoma from other solid tumors having similar appearances based upon molecular features, i.e. DNA sequences, of alveolar rhabdomyosarcoma. Distinguishing alveolar rhabdomyosarcoma from other tumors by examining them at the nucleic acid sequence level provides a more efficient means to identify the type of tumor. Such techniques are more reliable. Furthermore, the procedures of the invention can be used to detect the presence of small amounts of alveolar rhabdomyosarcoma in tissue. The invention provides a substantially more sensitive means of detecting the presence of alveolar rhabdomyosarcoma cells than that which is presently available.

It has been discovered that the translocation breakpoint on chromosome 2 consistently occurs within a specific region: the intron between the penultimate and the last exon of the PAX3 gene. Thus, the resulting translocation DNA sequence that contains the 5' portion of the PAX3 gene contains all of the PAX3 exons except the last one while the resulting translocation DNA sequence that contains the 3' portion of the PAX3 gene contains only a single PAX3 exon, the last one. It has been discovered that the translocation generates two new DNA sequences which are referred to herein as "chimeric genes". As used herein, "chimeric DNA sequence" refers to a DNA sequence of a chimeric gene.

Transcription products of the chimeric genes will be the same regardless of where in the intron the breakpoint occurs since intron sequences are removed by RNA splicing and the flanking exons juxtaposed in the spliced mRNA product. Therefore, although the breakpoint can occur at numerous places in the intron and different tumor cells will have different genomic sequences, mRNA and cDNA produced therefrom will always contain the same sequences of PAX3 origin.

It has been observed in each examined case of t(2;13) translocation, that the transcription product of the chimeric gene consistently contains the same sequence contributed by the gene on chromosome 13. The gene of chromosome 13, which has not been identified, is hereinafter referred to as the "chromosome 13 partner gene".

The present invention relates to methods of determining whether a tumor is an alveolar rhabdomyosarcoma tumor which comprise detecting the presence of a DNA sequence of a chimeric gene generated by translocation of a portion of human chromosome 2 and a portion of human chromosome 13. The presence of such a sequence indicates that the tumor is alveolar rhabdomyosarcoma.

In addition, the present invention relates to diagnostic kits for determining whether a tumor is an alveolar rhabdomyosarcoma tumor.

The present invention relates to isolated nucleic acid molecules and analogs which comprise a nucleotide sequence that is complementary to at least a portion of human chromosome 2 or a portion of human chromosome 13.

Furthermore, the present invention relates to monoclonal antibodies specific for a fusion protein encoded by the chimeric gene generated by the translocation involving a portion of human chromosome 2 and a portion of human chromosome 13 which causes alveolar rhabdomyosarcoma.

Another aspect of the present invention relates to transgenic animals that comprise a transgene which includes a chimeric gene generated by the translocation involving a portion of human chromosome 2 and a portion of human chromosome 13 which causes alveolar rhabdomyosarcoma.

DETAILED DESCRIPTION OF THE INVENTION

Translocation of chromosomal material between chromosome 2 and 13 has been associated with alveolar rhabdomyosarcoma. The t(2;13) translocation forms two chimeric genes: one having the 5' portion of a gene on chromosome 2 linked to the 3' portion of a gene from chromosome 13; the other having the 5' portion of a gene from chromosome 13 linked to the 3' portion of a gene from chromosome 2.

Identification of the genetic loci disrupted by the t(2;13) translocation has permitted the development of sequence-based assays for use in clinical diagnosis. There several reported sequence-based diagnostic assays which are used to detect the presence of chimeric genes that are generated by other chromosomal translocations. These reports, listed below and incorporated herein by reference, disclose clinical methods of detecting translocations using PCR techniques. In particular, these reports disclose methods of detecting chimeric DNA sequences when present in extremely small quantities.

Crescenzi, M. et al., (July 1988), *Proc. Natl. Acad. Sci. USA* 85:4869–4873 report PCR amplification of t(14;18) chromosome breakpoint translocations. A method of detecting minimal residual disease is disclosed using PCR techniques to amplify chimeric DNA sequences.

Lee, M. et al., (July 1987), *Science* 175–178 report PCR amplification of chimeric DNA sequences which occur in t(14;18) translocations but not in normal cells. This method is used for the detection of minimal residual cells carrying the chimeric gene.

Lee, M. et al., (1988) *Blood* 72(3):893–897 disclosed its detection of minimal residual BCR/ABL transcripts by modified polymerase chain reaction.

Sawyers, C. L. et al., (1990) *Proc. Natl. Acad. Sci. USA* 87:563–567 refer to a method of detecting relapse in chronic myelogenous leukemia patients after bone marrow transplantation using PCR. A PCR-based assay is used to detect the chimeric messenger RNA from BCR/ABL translocation.

Kawasaki, E. S. et al., (1988), *Proc. Natl. Acad. Sci. USA* 85:5698–5702 refer to a PCR-based diagnostic assay to detect chronic myeloid and acute lymphocytic leukemias using PCR. A PCR assay for detecting fused BCR/ABL chimeric genes which are the result of the Philadelphia translocation t(9;22) is disclosed.

Regarding the present invention, studies of the t(2;13) (q35;q14) translocation in alveolar rhabdomyosarcoma have localized the chromosome 2 breakpoint to a small mapping interval. The PAX3 gene is located within this interval and is rearranged in t(2;13)-containing tumor lines. The rearrangement breakpoints occur within an intron downstream of the paired-box and homeodomain-encoding regions. Upstream PAX3 sequences hybridize to a novel transcript in t(2;13)-containing lines. Cloning and characterization of this novel transcript indicate that this translocation juxtaposes the PAX3 DNA binding elements with the chromosome 13 partner gene sequences, suggesting formation of a hybrid transcription factor.

A genomic mapping strategy was employed to narrow down the regions on chromosome 2 and 13 that contain the t(2;13) breakpoints (see Barr, F. G., et al., (1991) *Genomics* 11:941 and Barr, F. G. et al., (1992) *Genomics*, 13:1150, both of which are incorporated herein by reference). For chromosome 2, numerous sequences were located with respect to the alveolar rhabdomyosarcoma t(2;13) breakpoint and a panel of other 2q rearrangements localized (see Barr, F. G. et al., (1992) *Genomics*, 13:1150). The resulting physical map of the distal 2q region revealed that the t(2;13) breakpoint is located within a genomic interval flanked by the inhibin α and intestinal alkaline phosphate loci.

The PAX3 gene is a human gene containing sequences homologous to the paired-box, a highly conserved domain implicated in transcriptional control of development (see Burri, M., et al., (1989) *EMBO J.* 8:1183, which is incorporated herein by reference). Cloning and analysis of the murine homologue Pax-3 revealed both paired-box and homeodomains in the 5' half of the gene with associated DNA binding activity (see Goulding, M. D. et al., (1991) *EMBO J.* (1991) 10:1135). Murine Pax-3 has been mapped by linkage to the region between the inhibin α and intestinal alkaline phosphatase loci on proximal mouse chromosome 1, which is syntenic with distal human 2q (see Epstein, D. J. et al., (1991) *Cell* 67:767).

Figure 1A:
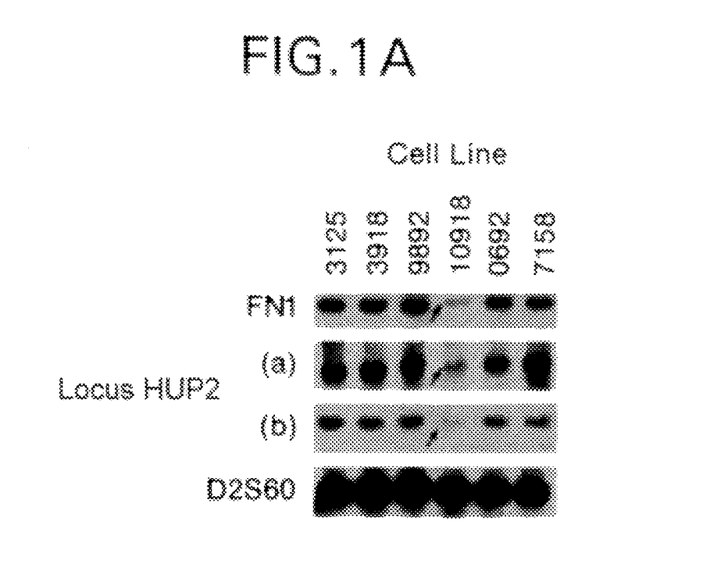
FIG. 1A shows the results of hybridization of a PAX3 intronic sequence and a murine Pax-3 cDNA fragment to genomic DNA from cell lines with deletions and unbalanced translocations of distal human 2q.

The PAX3 gene which occurs on chromosome 2 was investigated to determine whether that gene is involved in translocation. Hybridization of a PAX3 intronic sequence and a murine Pax-3 cDNA fragment to genomic DNA from cell lines with deletions and unbalanced translocations of distal human 2q demonstrated deletion of the PAX3 gene in cell line GM10918 (FIG. 1A). These data localize the PAX3 gene within physical mapping interval 6 on the distal 2q map (FIG. 1C), which is consistent with prior data which indicated localization of the t(2;13) breakpoint (Barr, F. G. et al., (1992) *Genomics*, 13:1150).

Involvement of the PAX3 gene in the t(2;13) translocation was further demonstrated using somatic cell hybrids that contain either the derivative chromosome 13 (der(13)) or the derivative chromosome 2 (der(2)) of the t(2;13) translocation. Oligonucleotide primers specific for the 5' and 3' regions of the PAX3 gene were designed based upon the published 5' genomic sequence (see Burri, M. (1989) *EMBO J.* 8:1183) and from the sequence of a 3' cDNA clone, respectively. With respect to the 3'-cDNA clone, a single positive plaque was isolated after screening 1,000,000 plaques from a human fetal brain cDNA library (Stratagene) with the Pax-3 cDNA probe. The isolated cDNA clone contained 640 bp from the 3' end of the PAX3 gene.

Figure 1B:
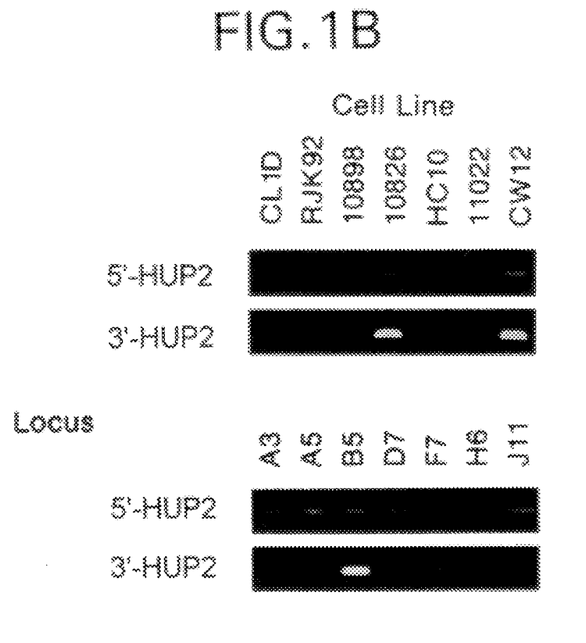
FIG. 1B shows results of amplification of somatic cell hybrid genomic DNA with oligonucleotide primers specific for the 5' and 3' regions of the PAX3 gene.
Figure 1C:
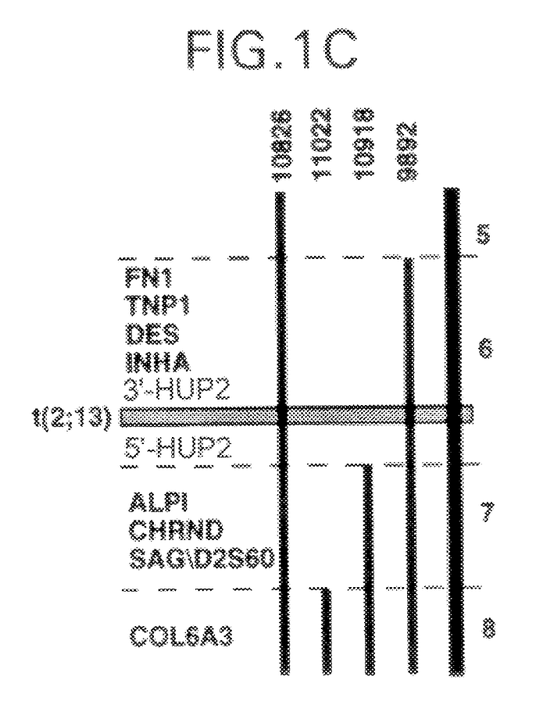
FIG. 1C shows a physical map of a distal region of chromosome 2.

Amplification of somatic cell hybrid genomic DNA with these primers demonstrated the presence of the 5' PAX3 region on the der(13) and the 3' PAX3 region on the der(2) (FIG. 1B). These findings indicate that the PAX3 gene is split by the t(2;13) translocation.

Figure 2A:
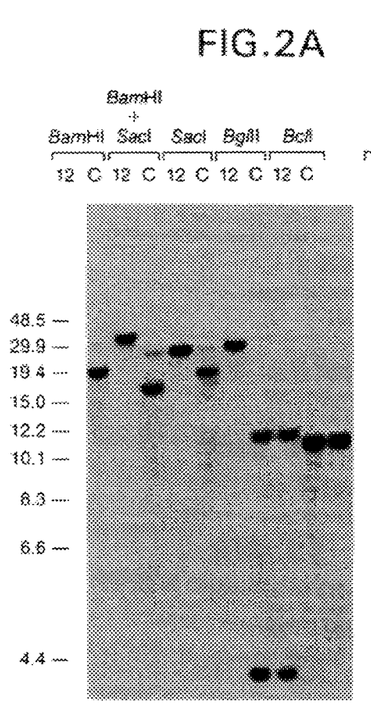
FIG. 2A shows the hybridization pattern of a Pax-3 cDNA fragment probe to restriction digests of CW12 tumor DNA and an unrelated lymphoid control line.

Rearrangement of the PAX3 gene was further investigated by Southern blot analysis of genomic DNA from rhabdomyosarcoma cell lines. The Pax-3 cDNA hybridizes to an additional fragment in BamHI and SacI digests of CW12 tumor DNA when compared with an unrelated lymphoid control line (FIG. 2A.). Identical results were obtained with lymphocyte DNA from patient CW12, thus ruling out restriction fragment length polymorphisms. This finding of tumor-specific fragments in multiple restriction endonuclease digests indicates the presence of a genomic rearrangement. The generality of PAX3 gene rearrangements in association with the t(2;13) is established by the presence of rearranged PAX3 gene fragments in two additional t(2;13)-containing rhabdomyosarcoma lines, Rh28 and Rh30 (FIG. 1B).

Figure 2B:
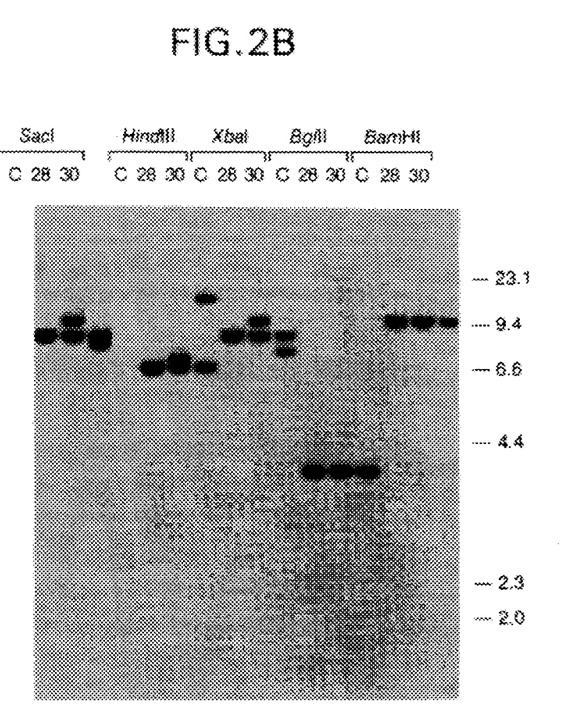
FIG. 2B shows the hybridization pattern of a Pax-3 cDNA fragment probe to restriction digests of an unrelated lymphoid control line, and Rh28 and Rh30 tumor DNA.
Figure 3:
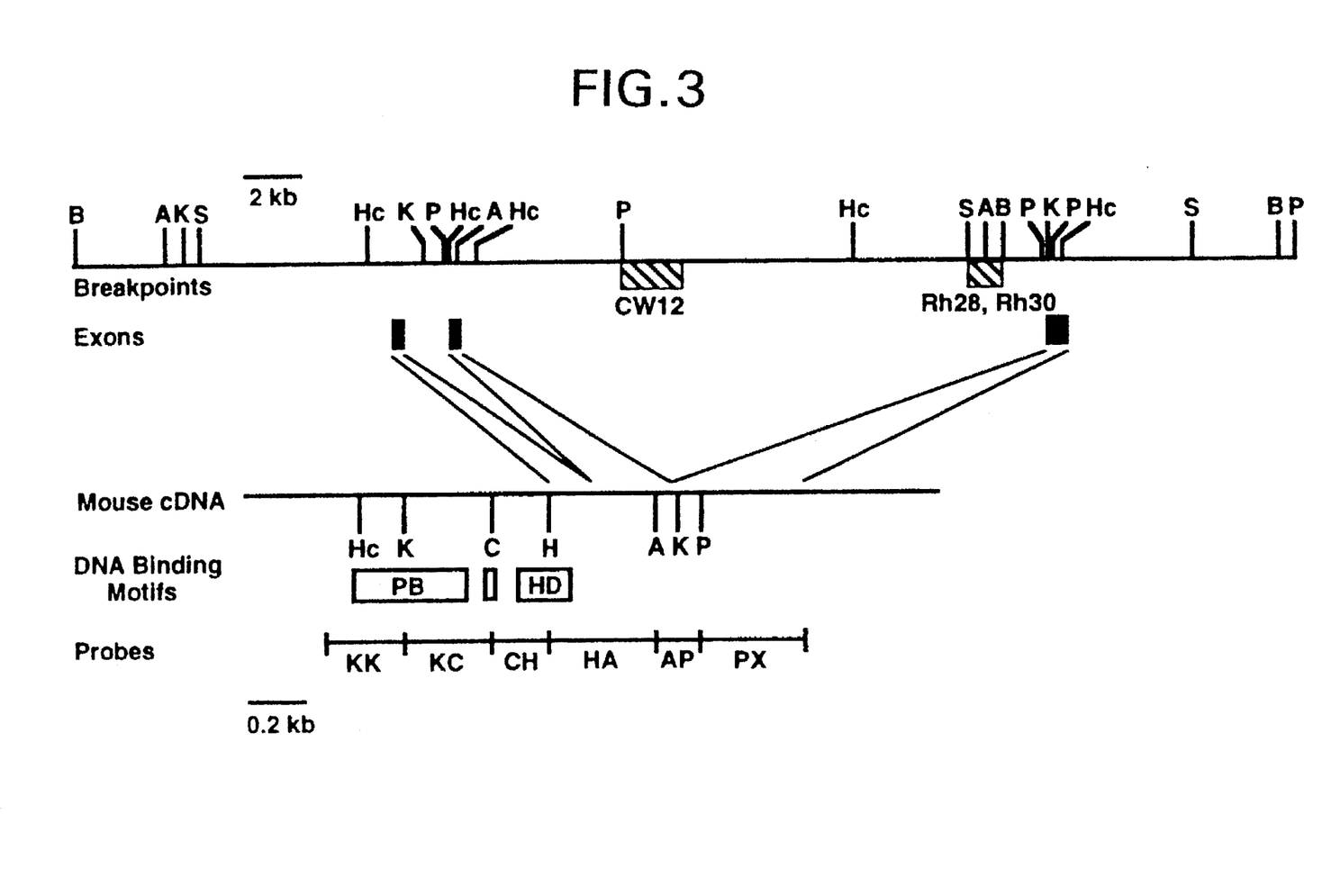
FIG. 3 shows a long-range restriction fragment map of the region surrounding the t(2;13) breakpoints.

To identify the region of the PAX3 gene disrupted by the rearrangement, the Pax-3 cDNA was divided into six fragments: (from 5' to 3') KpnI-KpnI, KpnI-ClaI, ClaI-HindIII, HindIII-ApaI, ApaI-PstI, and PstI-XbaI (FIG. 3). Each fragment was hybridized to the tumor/normal Southern blots. The rearrangement in CW12 was detected by the HindIII-ApaI and ApaI-PstI probes whereas the rearrangements in Rh28 and Rh30 were detected principally by the ApaI-PstI and PstI-XbaI probes (FIG. 2). Therefore, the rearrangements occur in the 3' region of the PAX3 gens, and the Rh28 and Rh30 breakpoints occur 3' relative to the CW12 breakpoint.

A long-range restriction map of the region surrounding the breakpoints in these rhabdomyosarcoma lines was then constructed (FIG. 3). Hybridization of the ApaI-PstI probe (which detects all three rearrangements) to multiple restriction digests of unrearranged DNA demonstrated two hybridizing bands, one of which also hybridizes to the HindIII-ApaI probe and the other hybridizes to the PstI-XbaI probe (data not shown). These findings are consistent with the presence of at least two exons in this region. The PAX3 cDNA sequence revealed that the ApaI and PstI sites in the Pax-3 cDNA are conserved in the human gens and thus mark separate PAX3 exons. The PAX3 sequence also identified HincII and NdeI sites 3' of the PstI site. Restriction maps were developed around each of these exons by digesting unrearranged DNA with ApaI or HincII and a second enzyme and hybridizing with the Pax-3 cDNA subfragments (FIG. 3).

The translocation breakpoints were localized by Southern blot analysis of DNA from the tumor lines. Analysis of cell line CW12 with the HindIII-ApaI probe revealed a rearranged fragment with SacI and BamHI but not PstI, thereby localizing the breakpoint to the SacI-PstI interval (FIGS. 2A and 3). The 16.5 kb size of the rearranged BamHI-SacI fragment further facilitated mapping of the CW12 breakpoint within 2 kb of the PstI site. For cell lines Rh28 and Rh30, hybridization with the PstI-XbaI probe revealed a rearranged fragment in SacI digests but not BamHI digests (FIG. 2B). In contrast, the HindIII-ApaI probe detects rearranged fragments in BamHI digests of Rh28 and Rh30 but not SacI digests (data not shown). These breakpoints thus occur between the BamHI and SacI sites (FIG. 3), and since this interval is detected by probes containing each exon, these BamHI and SacI sites serve to bridge the restriction maps around the ApaI- and PstI-containing exons.

This long range restriction map demonstrates that there is a 20 kb intron between the penultimate and final exon of the PAX3 gene. All three examined t(2;13) breakpoints are located within this intron. The Rh28 and Rh30 breakpoints are closely clustered in a 1 kb region 2 kb 5' to the last exon. The CW12 breakpoint is located further upstream 6 kb 3' of the penultimate exon. Different rearrangements within the same intron will result in the same alteration of the integrity of the PAX3 transcription unit. Furthermore, this intron is located 3' to the PAX3 paired-box and homeodomain-encoding regions and thus, the DNA binding domain remains intact.

Figure 4A:
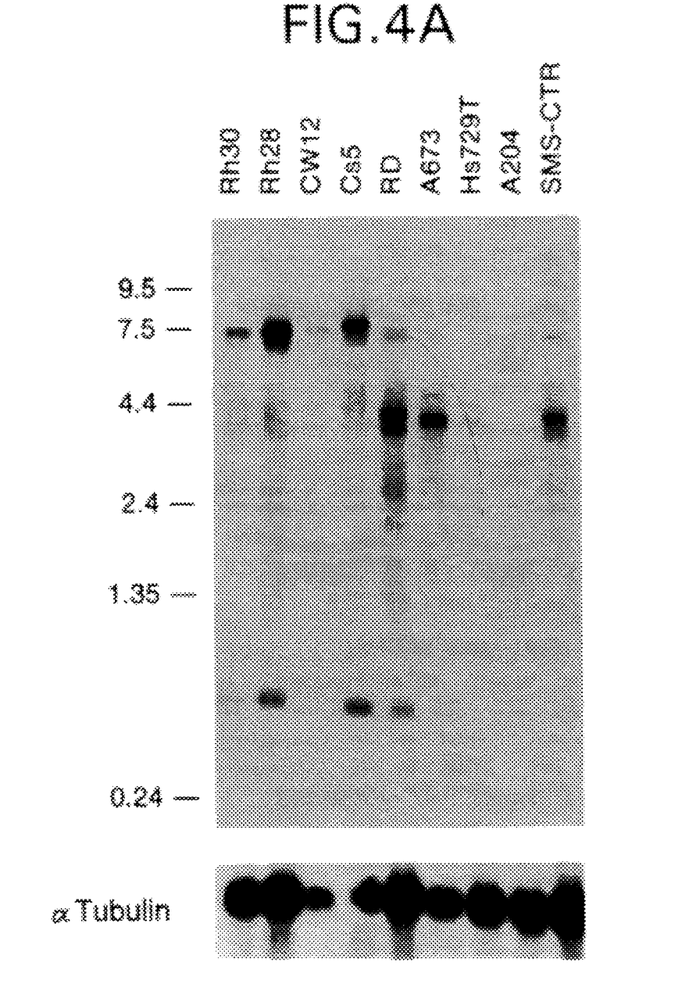
FIGS. 4A show results from Northern blot analysis of rhabdomyosarcoma cell lines, with a Pax-3 cDNA probe, a chromosome 13 partner DNA probe, and a control probe, respectively.

The alterations in gene expression associated with the t(2;13) translocation were investigated by Northern blot analysis of rhabdomyosarcoma cell lines (FIG. 4A). Hybridization of the Pax-3 cDNA to RNA from tumor lines that do not contain the t(2;13) reveals prominent bands between 3.5 and 4.5 kb as well as a lower band at 0.5 kb and a diffuse higher band at 6.6 kb. This diffuse 6.6 kb band does not hybridize to the HindIII-ApaI probe and thus may correspond to transcripts from another paired-box containing gene. The bands around 4 kb are similar to those reported in studies of Pax-3 expression during mouse development (Goulding, M. D., et al., (1991) *EMBO J.* 10:1135), and probably represent the wild-type PAX3 transcripts. In the t(2;13)—containing tumor lines, these bands are present but are weaker in intensity. However, a new intense 7.2 kb transcript is expressed in these t(2;13)-containing lines. This 7.2 kb mRNA hybridizes to the HindIII-ApaI but not the PstI-XbaI probe and thus this transcript only contains sequences 5' to the t(2;13) breakpoint. These findings indicate the formation of a novel transcript containing the PAX3 DNA binding elements that are now separated from 3' PAX3 domains. Though this novel transcript is probably initiated from the PAX3 promoter, the higher expression level relative to the presumed wild-type PAX3 transcript in the same cells suggests that additional positive regulatory elements are present or that negative regulatory elements were removed.

To further investigate the novel 7.2 kb transcript, a random-primed cDNA library from the t(2;13)—containing Rh28 rhabdomyosarcoma cell line was constructed. After screening this library with the Pax-3 cDNA probe, a clone which contained the expected PAX3 exons 5' to the t(2;13) breakpoint fused to a novel sequence was identified. This novel sequence was localized on a chromosome 13 mapping panel to 13q14 and further sublocalized to the appropriate physical interval which contains t(2;13) breakpoint. Northern blot analysis with this chromosome 13 sequence revealed a 6.5 kb band in most rhabdomyosarcoma lines and a second 7.2 kb band in the t(2;13)—containing lines (FIG. 4B). This 7.2 kb band exactly coincides with the band detected by the 5' PAX3 probes. These findings demonstrate that the result of the t(2;13) translocation is a chimeric transcript composed of 5' PAX3 sequences fused to RNA transcribed from a chromosome 13q14 locus.

These findings indicate that the t(2;13) translocation fuses the 5' region of the PAX3 gene to the 3' region of a gene on chromosome 13, and are consistent with the hypothesis that a chimeric transcription factor with novel properties is formed. These properties may result from removal of PAX3 regulatory domains and juxtaposition of the PAX3 DNA binding domain with new effector or protein interaction domains. Alternatively, the fusion protein that results from expression of the chimeric gene containing the 5' end of the chromosome 13 partner gene fixed to the 3' end of PAX3 may be responsible for the transformed state of cells having the t(2,13) translocation. However, the corresponding mRNA was not detected by Northern blot analysis. It is reasonable to hypothesize that a fusion protein is formed and is encoded by the chimeric gene containing the 5' portion of the PAX3 gene linked to the 3' portion of the chromosome 13 partner gene.

Gene fusions have been previously reported to be the basis of the t(1;19) in acute pre-B cell leukemia, the t(9;22) in chronic myelogenous leukemia, and the t(15;17) in acute promyelocytic leukemia (Cleary, M. L., (1991) Cell 66:619; Rabbits, T. H., (1991) Cell 67:641). In particular, the t(1;19) produces a chimeric transcription factor by fusing the homeobox DNA binding domain of the PBX gene with the transcriptional regulatory and protein dimerization domains of the E2A gene.

The localization of the breakpoint allows for the sequence-based molecular identification of the t(2;13) translocation and thereby identification of alveolar rhabdomyosarcoma. That is, rather than performing a visual inspection of the chromosomes, identification of the translocation between chromosome 2 and 13 can be performed by detecting the presence of DNA sequence associated with the chimeric genes. Preferred methods according to the present invention include the detection of the chimeric gene which contains the 5' end of the PAX3 gene linked to the 3' end of the chromosome 13 partner gene. The presence of the chimeric gene indicates that the tumor is alveolar rhabdomyosarcoma.

Aspects of the present invention include various methods of determining whether a tumor is alveolar rhabdomyosarcoma by sequence-based molecular analysis. Several different methods are available for doing so including those using Polymerase Chain Reaction (PCR) technology, restriction fragment length analysis using Southern blot technology, oligonucleotide hybridization technology, and in situ hybridization technology. Furthermore, the invention relates to probes, oligonucleotide primers, and monoclonal antibodies used in the methods of identifying alveolar rhabdomyosarcoma. In addition, the invention relates to diagnostic kits which comprise such components.

Alveolar rhabdomyosarcoma can be distinguished from non-alveolar rhabdomyosarcoma by identifying the presence of DNA sequences that occur only in alveolar rhabdomyosarcoma cells. These DNA sequences are the result of the translocation and are not present in non-alveolar rhabdomyosarcoma cells. As disclosed herein, it is now known that as a result of translocation, two chimeric genes are formed: one that contains the 5' portion of the PAX3 gene linked to the 3' portion of the chromosome 13 partner gene and another that contains the 5' portion of the chromosome 13 partner gene linked to the 3' portion of the PAX3 gene. Thus, sequence-based assays can be performed to identify whether or not these chimeric genes are present in a sample. Their presence indicates alveolar rhabdomyosarcoma. Furthermore, as disclosed herein, it is known that the chimeric gene which comprises the 5' portion of the PAX3 gene linked to the 3' portion of the chromosome 13 partner gene is transcribed. Thus, detection of the transcription product allows for the identification of alveolar rhabdomyosarcoma.

The sequence-based methods for determining the nature of tumors include but are not limited to polymerase chain reaction technology, restriction fragment length analysis using Southern blot technology, in situ hybridization technology and oligonucleotide hybridization technology. Each of these methods are useful to distinguish alveolar rhabdomyosarcoma from non-alveolar rhabdomyosarcoma by detecting, in one way or another, the presence of the chimeric genes or chimeric transcript that are only present as the result of the t(2;13) translocation. The methods described herein are meant to exemplify how the present invention may be practiced and are not meant to limit the scope of invention. It is contemplated that other sequence-based methodology for detecting the presence of specific nucleotide sequences can be used to distinguish alveolar rhabdomyosarcoma from non-alveolar rhabdomyosarcoma as taught by the present invention.

A preferred method to identify alveolar rhabdomyosarcoma is to detect the presence of specific DNA sequences in genetic material derived from cells suspected of being alveolar rhabdomyosarcoma using polymerase chain reaction (PCR) technology. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. Some simple rules aid in the design of efficient primers. Typical primers are 18–28 nucleotides in length having 50% to 60% g+c composition.

PCR technology allows for the rapid generation of multiple copies of DNA sequences by providing 5' and 3' primers that hybridize to sequences present in a DNA molecule, and further providing free nucleotides and an enzyme which fills in the complementary bases to the DNA sequence between the primers with the free nucleotides to produce a complementary strand of DNA. The enzyme will fill in the complementary sequences adjacent to the primers. If both the 5' primer and 3' primer hybridize to DNA sequences on the same small fragment of DNA, exponential amplification of a specific double-stranded size product results. If only a single primer hybridizes to the DNA fragment, linear amplification produces single-stranded products of variable length.

In the present invention, alveolar rhabdomyosarcoma can be identified by detecting a chimeric gene that results from the t(2;13) translocation preferably, by detecting the chimeric transcript present in alveolar rhabdomyosarcoma which contains the 5' portion of the PAX3 gene linked to the 3' portion of the chromosome 13 partner gene. This is accomplished performing PCR on a sample of genetic material derived from cells suspected of being alveolar rhabdomyosarcoma using PCR primers that hybridize to the 5' end of PAX3 and the 3' end of the chromosome 13 partner gene or to the 5' end of the chromosome 13 partner gene and the 3' end of PAX3. If an alveolar rhabdomyosarcoma-specific chimeric gene is present, it will be amplified.

To perform this method, RNA is extracted from tumor cells and used to make cDNA using well known methods and readily available starting materials. PCR can be performed on genomic DNA instead of cDNA derived from RNA. However, because the breakpoint occurs at variable locations in an intron, the resulting chimeric genomic fragment will also be variable. Because of the large size of the intron, a large number of oligonucleotide primers would have to be tested in order to efficiently and successfully amplify a chimeric genomic fragment. It is therefore easier and preferred to use cDNA although it is technically possible and therefore contemplated that the method can be performed using genomic DNA.

The cDNA is combined with the primers, free nucleotides and enzyme following standard PCR protocols. The mixture undergoes a series of temperature changes. If the cDNA of the chimeric gene is present, that is, if both primers hybridize to sequences on the same molecule, the molecule comprising the primers and the intervening complementary sequences will be exponentially amplified. The amplified DNA can be easily detected by a variety of well known means. If the chimeric gene is not present, no DNA molecule will be exponentially amplified. Rather, amplification of wild-type transcript will yield low levels of variable length product. The PCR technology therefore provides an extremely easy, straightforward and reliable method of detecting the chimeric gene.

When using cDNA, primers that hybridize to the 5' portion of the PAX3 gene and the 3' portion of the chromosome 13 partner gene are used. RNA comprising the 5' portion of the chromosome 13 partner gene and the 3' portion of PAX3 have not been detected thus far. Accordingly, while it is contemplated that cDNA containing the 5' portion of chromosome 13 partner gene linked to the 3' portion of PAX3 can be the subject of PCR to identify alveolar rhabdomyosarcoma, only the transcript encoding the 5' portion of the PAX3 gene and the 3' portion of the chromosome 13 partner gene is used pending confirmation of that both chimeric genes are transcribed.

Accordingly, a preferred method of determining whether a cell is alveolar rhabdomyosarcoma is by using PCR technology on cDNA to detect the presence of a chimeric gene that contains the 5' portion of the PAX3 gene and the 3' portion of the chromosome 13 partner gene. The presence of the chimeric gene indicates that the tumor is alveolar rhabdomyosarcoma. Sets of primers are prepared which consist of primers that hybridize to the 5' end of PAX3 and the 3' end of chromosome 13 partner gene. Primers may be designed based upon the sequence disclosed in SEQ ID 1 and SEQ ID 2. The preferred primers are disclosed as SEQ ID 3 and SEQ ID 4. If the chimeric gene is present, multiple copies of the cDNA transcribed from it will be made. If the chimeric gene is not present, PCR will not generate a discrete detectable product. Amplified DNA may be detected by several well known means. The preferred method for detecting the presence of amplified DNA is to separate the PCR reaction material by gel electrophoresis and stain the gel with ethidium bromide in order to visual the amplified DNA if present. A size standard of the expected size of the amplified DNA is preferably run on the gel as a control.

In some instances, such as when unusually small amounts of RNA are recovered and only small amounts of cDNA are generated therefrom, it is desirable or necessary to perform a PCR reaction on the first PCR reaction product. That is, if difficult to detect quantities of amplified DNA are produced by the first reaction, a second PCR can be performed to make multiple copies of DNA sequences of the first amplified DNA. A nested set of primers are used in the second PCR reaction. The nested set of primers hybridize to sequences downstream of the 5' primer and upstream of the 3' primer used in the first reaction.

The present invention includes oligonucleotides which are useful as primers for performing PCR methods to amplify chimeric genes generated by the t(2;13) translocation. Accordingly, the present invention includes PCR primers that hybridize to the 5' end of PAX3 and the 3' end of the chromosome 13 partner gene or to the 5' end of the chromosome 13 partner gene and the 3' end of PAX3. Preferably, the PCR primers of the present invention include PCR primers that hybridize to the 5' end of PAX3 and the 3' end of the chromosome 13 partner gene. More preferably, PCR primers of the present invention are designed based upon the sequence disclosed in SEQ ID 1 and SEQ ID 2. The preferred primers are disclosed as SEQ ID 3 and SEQ ID 4.

According to the invention, diagnostic kits can be assembled which are useful to practice methods of distinguishing alveolar rhabdomyosarcoma tumors from non-alveolar rhabdomyosarcoma tumors. Such diagnostic kits comprise oligonucleotides which are useful as primers for performing PCR methods to amplify chimeric genes generated by the t(2;13) translocation. Accordingly, diagnostic kits of the present invention comprise PCR primers that hybridize to the 5' end of PAX3 and the 3' end of the chromosome 13 partner gene or to the 5' end of the chromosome 13 partner gene and the 3' end of PAX3. Preferably, the diagnostic kits of the present invention comprise PCR primers that hybridize to the 5' end of PAX3 and the 3' end of the chromosome 13 partner gene. More preferably, diagnostic kits of the present invention comprise PCR primers that are designed based upon the sequence disclosed in SEQ ID 1 and SEQ ID 2. The preferred diagnostic kit of the present invention comprises PCR primers as disclosed as SEQ ID 3 and SEQ ID 4. It is preferred that diagnostic kits according to the present invention comprise a size marker to be run as a standard on a gel used to detect the presence of amplified DNA. The size marker is the same size as the DNA generated by the primers in the presence of the chimeric gene.

In addition to diagnosis, the PCR methodology and PCR-based kits are particularly useful for monitoring the disease once the diagnosis is established. In particular, the sensitivity of the PCR assay permits detection of small amounts of tumor for purposes of staging the patient, determining response to therapy and predicting early relapse.

Another method of determining whether a cell is alveolar rhabdomyosarcoma is to perform restriction fragment length analysis of genomic DNA. A Southern blot of cellular DNA that has been cut with restriction enzymes is contacted with probes that hybridize to DNA sequences adjacent to the translocation breakpoint. The pattern formed when segments of the DNA that are cut with restriction enzymes, separated by electrophoresis, fixed to blotting medium and probed with fragments that hybridize to sequences adjacent to the translocation breakpoint is known for DNA in which no translocation has taken place. Therefore, if the resulting pattern differs from the expected pattern, translocation and, thus, alveolar rhabdomyosarcoma is indicated.

The techniques for performing restriction fragment length analyses are well known by those having ordinary skill in the art. DNA extraction, restriction enzyme digestion, electrophoresis, Southern blotting, probe preparation and hybridization are all well known techniques that can be routinely performed using readily available starting material.

According to the invention, the information identifying the area where the breakpoint occurs together with the extensive restriction fragment map of the DNA molecule thereabout provide sufficient information to allow one having ordinary skill in the art to devise protocols for doing Southern blot analysis to identify alveolar rhabdomyosarcoma with only routine experimentation using well established techniques. The present invention allows one having ordinary skill in the art to choose restriction enzymes to be used in digestion of DNA being tested and to synthesize or isolate probes from clonal material, the probes being useful to distinguish translocated from untranslocated DNA.

FIG. 3 provides information regarding structure of both the PAX3 genomic gene and the PAX3 cDNA. As shown, the alveolar rhabdomyosarcoma breakpoint occurs in the intron between the penultimate and the last exon of the PAX3 gene. An extensive restriction enzyme map of the genomic DNA is provided at the top portion of FIG. 3 and the fragments generated by various enzymes or combinations of enzymes are predictable. The pattern made by such cleaved fragments when separated using gel electrophoresis is also predictable.

One having ordinary skill in the art, performing routine techniques, could select enzymes to generate fragments from genomic DNA extracted from a tumor. The fragments are separated by electrophoresis and, for example, transferred to nitrocellulose paper. Labelled probes made from an isolated specific fragment or fragments can be used to visualize the presence of a complementary fragment fixed to the paper.

Probes can be produced which contain only sequences from exons that are either 5' or 3' of the PAX3 intron where the breakpoint occurs. These probes can be used as described above to analyze restriction enzyme patterns and determine whether or not the translocation has occurred. Generally, DNA fragments used as probes are isolated from cloned material. The cloned fragments can vary in size but are usually larger than oligonucleotides used in PCR; preferably they are between about 100 and about 500 bp.

One having ordinary skill in the art can use the information presented in restriction enzyme map shown in FIG. 3 and perform well known techniques to analyze genetic material to detect the presence of chimeric genes. Using the information disclosed herein and routine methods, one having ordinary skill in the art can now use restriction fragment length analysis techniques to determine whether or not a patient has alveolar rhabdomyosarcoma. The preferred restriction enzymes for use in Southern blot restriction fragment analysis include at least one of the enzymes selected from the group consisting of SacI, BamHI, KpnI, and ApaI. These may be used separately, in combination with each other, or in combination with other enzymes. Similarly, other enzymes may be used separately or in combination to the exclusion of the preferred enzymes.

The critical factor is to generate a distinguishable restriction pattern which will occur in untranslocated DNA probed with a fragment that hybridizes to a DNA sequence either upstream or downstream of the breakpoint region. This restriction pattern must be repeatable. When DNA that has undergone translocation is tested, the same restriction enzyme digestions produces a pattern different from the expected pattern; usually novel bands super-imposed on a wild-type pattern. The different pattern indicates translocation. Following the teachings of the invention, Southern blot analysis of restriction fragment lengths is an effective way to diagnose alveolar rhabdomyosarcoma.

The present invention includes fragments which are useful as probes for performing restriction fragment length analyses using Southern blot methods to identify DNA molecules that contain the t(2;13) translocation. Accordingly, the present invention includes probes that hybridize to DNA sequences adjacent to the t(2;13) breakpoints that occur in either the PAX3 or chromosome 13 partner gene. In particular, probes of the present invention preferably hybridize to DNA sequences in the penultimate exon of the PAX3 gene, which is upstream from the t(2;13) breakpoint, or to the last exon of the PAX3 gene, which is downstream from the t(2;13) breakpoint. Preferably, the probes of the present invention include are fragments isolated from cloned material which contain basepairs 9–165 and 198–602 of SEQ ID 1. These probes will hybridize to the 5' and 3' sides of the rearrangement respectively. Generally, the probes preferably hybridize to a DNA sequence of the PAX3 gene which is either upstream or downstream of the translocation breakpoint region. The probes are preferably labelled, most preferably labelled with a radioisotope.

According to the invention, diagnostic kits can be assembled which are useful to practice methods of distinguishing alveolar rhabdomyosarcoma tumors from non-alveolar rhabdomyosarcoma tumors by restriction fragment length analysis. Such diagnostic kits comprise cloned DNA fragments which are useful as probes for performing restriction fragment length analysis on Southern blots of DNA extracted from cells. Accordingly, diagnostic kits of the present invention comprise a cloned DNA fragment probe that hybridizes to a DNA sequence adjacent to a t(2;13) translocation breakpoint. Preferably, the diagnostic kits of the invention comprise probes that hybridize to DNA sequences in the penultimate exon of the PAX3 gene, which is upstream from the t(2;13) breakpoint, or to the last exon of the PAX3 gene, which is downstream from the t(2;13) breakpoint. Preferably, the diagnostic kits of the invention comprise probes that are designed based upon the sequence disclosed in SEQ ID 1 and SEQ ID 2. The preferred oligonucleotide probes comprises base pairs 9–165 and 198–602 of SEQ ID 1. The probes preferably hybridize to a DNA sequence of the PAX3 gene which is either upstream or downstream of the translocation breakpoint region. The probes are preferably labelled, most preferably labelled with a radioisotope. The diagnostic kits according to the present invention may further comprise a negative control to be run as a standard. The negative control is a DNA sample that produces the restriction pattern expected if translocation has not taken place. Thus, the pattern produced by the sample being tested can be compared side by side with the control. One would use genomic DNA from the patient's normal tissue as a negative control. If the pattern produced by the sample being tested is substantially identical to the control pattern, alveolar rhabdomyosarcoma is not indicated. If the pattern produced by the sample being tested is dissimilar to the control pattern, alveolar rhabdomyosarcoma is indicated.

Another method of detecting the presence of specific DNA sequences is by in situ hybridization technology. In situ hybridization technology is well known by those having ordinary skill in the art. Briefly, detectable probes which contain a specific DNA sequence are added to fixed cells or isolated nuclei. If the cells contain complementary nucleotide sequences, the probes, which can be detected, will hybridize to them. One having ordinary skill in the art, using the sequence information disclosed herein and the disclosure of the breakpoint location including adjacent genes can devise a variety of protocols that use in situ hybridization technology to identify alveolar rhabdomyosarcoma.

According to the preferred method of using in situ hybridization techniques to identify whether of not a cell in alveolar rhabdomyosarcoma, sets of probes are provided which comprise at least one probe that hybridizes to a portion of the PAX3 gene either upstream or downstream of the breakpoint and at least one probe that hybridizes to a portion of the chromosome 13 partner gene either upstream or downstream of the breakpoint. A set of probes comprises at least either the 5' PAX3 probe and 3' chromosome 13 partner gene probe or the 5' chromosome 13 partner gene probe and the 3' PAX3 probe. Each probe is labelled i for example, with a fluorescent marker; the PAX3 probes having a different color marker from the chromosome 13 probes. Alternatively, the two probes could be from the same gene. In this case, translocation would lead to wide separation of the two signals. For in situ hybridization, it is preferred that very large cloned fragments are used as probes. A common procedure is to label probe with biotin-modified nucleotide and then detect with fluorescently tagged avidin. Hence, probe does not itself have to be labelled with florescent but can be subsequently detected with florescent marker.

Cells are fixed or their nuclei are isolated and the probes are added to the genetic material. It is not necessary that the chromosome be visibly identifiable as in a karyotype. Probes will hybridize to the complementary nucleic acid sequences present in the sample. Using a fluorescent microscope, the probes can be visualized by their fluorescent markers.

Alveolar rhabdomyosarcoma can be identified by the manner in which the hybridized probes appear when observed. In cases where no t(2,13) translocation has taken place, the probes to different genes will hybridize to separate chromosomes which will be visible by their distinct color labels of the probes. If the t(2,13) translocation has taken place, the two different probes will hybridize adjacent to each other on the same chromosome. The probes will be visible as being very close to each other. The colors of the label will likely blend and appear as an intermediate color of the two used. If probes to the same gene are used, they will appear adjacent to each other if no translocation occurred and apparent from each other in cells with translocations.

The present invention includes labelled cloned fragments which are useful as probes for performing in situ methods to amplify chimeric genes generated by the t(2,13) translocation. The probes are distinguishable from each other. Accordingly, the present invention includes labelled probes that hybridize to the 5' end of PAX3 and the 3' end of the chromosome 13 partner gene or to the 5' end of the chromosome 13 partner gene and the 3' end of PAX3. Preferably, the labelled probes of the present invention include labelled probes that hybridize to the 5' end of PAX3 and the 3' end of the chromosome 13 partner gene. The labelled probes of the present invention are preferably labelled with fluorescent markers.

According to the invention, diagnostic kits can be assembled which are useful to practice in situ hybridization methods of distinguishing alveolar rhabdomyosarcoma tumors from non-alveolar rhabdomyosarcoma tumors. Such diagnostic kits comprise a set of labelled fragments which are useful as probes for performing in situ hybridization methods to visually distinguish chimeric genes generated by the t(2;13) translocation from genetic material that did not undergo the translocation. Accordingly, diagnostic kits of the present invention comprise a set of labelled probes that include a probe that hybridizes to the 5' end of PAX3 and a probe that hybridizes to the 3' end of the chromosome 13 partner gene or a probe that hybridizes to the 5' end of the chromosome 13 partner gene and a probe that hybridizes the 3' end of PAX3. Preferably, the diagnostic kits of the present invention comprise a set of labelled probes that include a probe that hybridizes to the 5' end of PAX3 and a probe that hybridizes the 3' end of the chromosome 13 partner gene. It is preferred that labelled probes of the in situ diagnostic kits according to the present invention are labelled with a fluorescent marker.

Another method of detecting the presence of specific DNA sequences is by oligonucleotide hybridization technology. Oligonucleotide hybridization technology is well known to those having ordinary skill in the art. Briefly, detectable probes which contain a specific nucleotide sequence that will hybridize to genetic material containing the t(2;13) translocation but which will not hybridize to genetic material that does not contain a chimeric gene which results from the t(2;13) translocation. The cell's RNA or cDNA made from RNA is fixed, usually to filter paper or the like. The probes are added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicate complementary sequences. One having ordinary skill in the art, using the sequence information disclosed herein and the disclosure of the breakpoint location including adjacent genes can devise a variety of protocols that use oligonucleotide hybridization technology to identify alveolar rhabdomyosarcoma.

According to the preferred method of using oligonucleotide hybridization techniques to identify whether of not a cell is alveolar rhabdomyosarcoma, a probe is provided which hybridizes to the chimeric transcript or cDNA thereof that comprises the 5' portion of the PAX3 gene and the 3' portion of the chromosome 13 partner gene but which will not hybridize to transcripts encoding wild-type PAX3 or chromosome 13 partner genes. The probe comprises the most downstream nucleotides of the 5' portion of PAX3 present in the chimeric gene and the most upstream nucleotides of the 3' portion of the chromosome 13 partner gene present in the chimeric gene. Thus, the probe hybridizes to the chimeric transcript at the location where the PAX3 sequences are linked to the chromosome 13 partner gene sequences. The probe is labelled with a radioisotope.

SEQ ID NO:5 contains part of the nucleotide sequence of the chimeric transcript that comprises the 5' portion of the PAX3 linked to the 3' portion of chromosome 13 partner gene. Nucleotide 165 and 166 of SEQ ID NO:5, are the linkage point between the PAX3 sequences and the chromosome 13 sequences.

RNA is extracted from cells and used to make cDNA. The cDNA is blotted to nitrocellulose or nylon filters and after treatment with prehybridizing buffer, probe is added for hybridization. The cDNA blot is then washed under conditions that are sufficiently stringent to permit hybridization to take place only if the probe is fully complementary to the cDNA. The chimeric cDNA is present if the probe remains hybridized after washing, indicating the translocation associated with alveolar rhabdomyosarcoma.

The present invention includes labelled oligonucleotides which are useful as probes for performing oligonucleotide hybridization methods to identify the t(2;13) translocation. Accordingly, the present invention includes labelled probes that hybridize to the chimeric sequence that comprises 5' end of PAX3 linked to the 3' end of the chromosome 13 partner gene. The labelled probes of the present invention are labelled with radiolabelled nucleotides or are otherwise detectable by readily available nonradioactive detection systems. Probes comprise oligonucleotides having a portion of the sequence of SEQ ID NO:6 including 165–166.

According to the invention, diagnostic kits can be assembled which are useful to practice oligonucleotide hybridization methods of distinguishing alveolar rhabdomyosarcoma tumors from non-alveolar rhabdomyosarcoma tumors. Such diagnostic kits comprise a labelled oligonucleotide which hybridizes to the chimeric transcript that results from the t(2;13) translocation but which does not hybridize to nucleic acid transcripts not associated with the translocation. Accordingly, diagnostic kits of the present invention comprise a labelled probe that includes the most downstream sequences of the 5' end of PAX3 and the most upstream sequences of the 3' end of the chromosome 13 partner gene which make up the chimeric transcript associated with t(2;13) translocation. Probes comprise oligonucleotides having a portion of the sequence of SEQ ID NO:5 including 165–166. It is preferred that labelled probes of the oligonucleotide diagnostic kits according to the present invention are labelled with a radionucleotide. The oligonucleotide hybridization-based diagnostic kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample.

In addition to sequence-based methods of identifying alveolar rhabdomyosarcoma tumors which express the t(2;13) rearrangement, the present invention relates to monoclonal antibody-based diagnostics. Monoclonal antibodies of the present invention are directed at the fusion protein which results from the translation of mRNA of the chimeric gene which comprises the 5' portion of PAX3 linked to the 3' portion of the chromosome 13 partner gene. Because the transcription product of that chimeric gene and not the other chimeric gene generated by translocation has been observed, the fusion protein that is encoded by the 5' PAX3/3' chromosome 13 partner gene sequences is the putative transformation agent. Monoclonal antibodies that bind to the fusion protein but that do not crossreact with the non-translocation protein products can be used to detect the presence of the fusion proteins and indicate chromosomal translocation. Monoclonal antibody-based kits which contain monoclonal antibodies that specifically bind to the fusion protein and control samples are within the scope of the present invention. One having ordinary skill in the art using standard techniques can generate such monoclonal antibodies and use them in an assay to detect fusion proteins.

In another aspect of the invention, transgenic animals, particularly transgenic mice, are generated. The transgenic animals according to the invention contain the chimeric gene of the t(2;13) rearrangement responsible for alveolar rhabdomyosarcoma. Such transgenic mice may be used as animal models for studying alveolar rhabdomyosarcoma and for use in drug discovery efforts to find compounds effective against alveolar rhabdomyosarcoma tumors. One having ordinary skill in the art using standard techniques, such as those taught in U.S. Pat. No. 4,873,191 issued Oct. 10, 1989 Wagner and U.S. Pat. No. 4,736,866 issued Apr. 12, 1988 to Leder, both of which are incorporated herein by reference, can produce transgenic animals which produce the alveolar rhabdomyosarcoma translocation fusion protein and use the animals in drug discovery projects.

EXAMPLE

A method of determining whether a tumor is an alveolar rhabdomyosarcoma tumor using PCR technology has been designed as follows. According to the method, RNA is extracted from cells being tested and is used to generate cDNA. PCR is performed on the cDNA to detect the presence of a chimeric transcript which contains the 5' portion of the PAX3 gene linked to the 3' portion of the chromosome 13 partner gene. Primers have been designed which hybridize to the portion of PAX3 cDNA between about 125 and about 175 base pairs upstream from the t(2;13) breakpoint on the PAX3 gene and to the portion of the chromosome 13 partner gene between about 200 to about 250 base pairs downstream from the t(2;13) breakpoint on the chromosome 13 partner gene. If a DNA sequence is amplified using the primers in a PCR reaction with the cDNA, the presence of a chimeric transcript and thus, alveolar rhabdomyosarcoma is indicated.

The primers 2CF3 (GCACTGTACACCAAAGCACG—SEQ ID NO:3) and 13R1 (AACTGTGATCCAGGGCTGTC—SEQ ID NO:4) were designed by the following means. Lists of possible primers were generated using the software program PRIMER version 0.5 (from Whitehead Institute) with the default search criteria (except for 24 bp maximum length and one 3' G/C residue). Primers which have melting temperature close to 60° C. and generate a product of 200–500 bp were then selected from the regions of the available sequence which were most accurate. By these means, primers 2CF3 and 13R1 listed above which generate a 410 bp product were selected.

For these experiments, poly(A)+RNA was prepared from cells using the Invitrogen FastTrack system. PCR experiments were performed with the Perkin Elmer Cetus Gene-AmpRNA PCR kit. The procedure consists of reverse transcription of the RNA with random hexamer primers. The 20 µl reverse transcription reaction volume contains 100 ng poly(A)+RNA, 1X PCR Buffer II, 5 mM $MgCl_2$, 1 mM of each dNTP, 1 U/µl RNase inhibitor, 2.5 U/µl reverse transcriptase, and 2.5 µM random hexamers. This reaction is incubated at 42° C. for fifteen minutes, 99° C. for five minutes and then cooled to 5° C. For PCR application of this cDNA, an additional 30 µl mixture containing PCR buffer II, 2CF3 and 13R1 primers, and Taq polymerase is added to give final reaction conditions of 1X PCR Buffer II, 1 mM of each primer (2CF3 and 13R1), and 0.025 U/µl Taq Polymerase. Cycling conditions consist of an initial 1.5 minute incubation at 94° C.; then 35 cycles of one minute at 94° C., one minute at 60° C., and three minutes at 72° C.; and a final 7 minute incubation at 72° C. Aliquots of the PCR reactions are electrophoresed on 2% agarose gels in Tri-Borate-EDTA buffer and stained with 0.5 µg/ml ethidium bromide. Sensitivity of this assay can be increased and the specificity of the product can be assayed further by Southern blot transfer of the gel to a nylon membrane (Hybond N+, Amersham), and hybridization with labeled probes (AP160 and 416RI) specific for the rearranged regions of the PAX3 gene and the chromosome 13 partner. AP160 is ApaI-PstI fragment of mouse Pax-3 cDNA shown in FIG. 3. A more appropriate probe would be cloned human PAX3 fragment corresponding to nt 9–165 of SEQ ID 1. 419RI is a 620 bp fragment from the cloned cDNA of the chromosome 13 partner gene corresponding to nt 1–620 in SEQ ID NO. 2.

The reaction sample is run on an agarose electrophoresis gel with a DNA fragment the size of the expected amplified DNA in an adjacent lane to serve as a control. The expected size of the DNA fragment amplified using primers 2CF3 and 13R1 and alveolar rhabdomyosarcoma cDNA is 410 basepairs. If a DNA sequence is amplified using the primers in a PCR reaction with the cDNA, the DNA molecule will run in the gel the same distance as the control.

A diagnostic kit is assembled which contains primers 2CF3 and 13R1 in at least one container and the 410 base pair DNA molecule that is useful as size standard in another container.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 645 base pairs
        ( B ) TYPE: nucleic acid
        ( C ) STRANDEDNESS: double
        ( D ) TOPOLOGY: linear     ( i i ) MOLECULE TYPE: cDNA     ( x i ) SEQUENCE DESCRIPTION: SEQ ID NO:1:

```
AGCACTGTAC  ACCAAAGCAC  GATTCCTTCC  AACCCAGACA  GCAGCTCTGC  CTACTGCCTC       60
CCCAGCACCA  GGCATGGATT  TTCCAGCTAT  ACAGACAGCT  TTGTGCCTCC  GTCGGGCCC       120
TCCAACCCCA  TGAACCCCAC  CATTGGCAAT  GGCCTCTCAC  CTCAGGTAAT  GGGACTCCTG      180
ACCAACCACG  GTGGGGTACC  TCATCAGCCC  CAGACTGATT  ACGCGCTCTC  CCCTCTCACC      240
GGGGGTCTGG  AACCTACCAC  CACGGTGTCG  GCCAGCTGCA  GTCAGAGACT  AGACCATATG      300
AAGAGCTTGG  ACAGTCTGCC  AACATCTCAG  TCCTACTGTC  CACCCACCTA  TAGCACCACA      360
GGCTACAGTA  TGGACCCTGT  CACAGGCTAC  CAATATGGGC  AGTATGGACA  AAGTAAGCCT      420
TGGACTTTTT  AGGGGCAAT   TCCTCCTGGA  AGGGAGATAA  ACTCAACTCT  TCCTTAAGAA      480
AGGTGAATTA  GAGGCAAGAT  TAAGCCACAC  ATGCCGGTAT  CAATTTTTT   TTTTTTTTT      540
GCAAAGCCAG  CTGACTGTTC  CAGCAGGGGC  TTCCTTGTGT  AATTATTTC   TTAACTGATG     600
TCAACAACAT  CTTGCGGTTA  TTAATTGTTG  AGACGTGAAA  CCTGA                      645
```

( 2 ) INFORMATION FOR SEQ ID NO:2:

( i ) SEQUENCE CHARACTERISTICS:
        ( A ) LENGTH: 620 base pairs
        ( B ) TYPE: nucleic acid
        ( C ) STRANDEDNESS: double
        ( D ) TOPOLOGY: linear     ( i i ) MOLECULE TYPE: cDNA     ( x i ) SEQUENCE DESCRIPTION: SEQ ID NO:2:

```
AATTCAATTC  GTCATAATCT  GTCCCTACAC  AGCAAGTTCA  TTCGTGTGCA  GAATGAAGGA       60
ACTGGAAAAA  GTTCTTGGTG  GATGCTCAAT  CCAGAGGGTG  GCAAGAGCGG  GAAATCTCCA      120
TGGAGAAGAG  CTGCATCCAT  GGACAACAAC  AGTAAATTTG  CTAAGAGCCG  AAGCCGAGCT      180
GCCAAGAAGA  AAGCATCTCT  CCAGTCTGGC  CAGGAGGGTG  CTGGGGACAG  CCCTGGATCA      240
CAGTTTTCCA  AATGGCCTGC  AAGCCCTGGC  TCTCACAGCA  ATGATGACTT  TGATAACTGG      300
```

| | | | | | |
|---|---|---|---|---|---|
| AGTACATTTC | GCCCTCGAAC | TAGCTCAAAT | GCTAGTACTA | TTAGTGGGAG | ACTCTCACCC | 360 |
| ATTATGACCG | AACAGGATGA | TCTTGGAGAA | GGGGATGTGC | ATTCTATGGT | GATCCCGCCA | 420 |
| TCTGCCGCAA | AGATGGCCTC | TACTTTACCC | AGTCTGTCTG | AGATAAGCAA | TCCCGAAAAC | 480 |
| ATGGAAAATC | TTTTGGATAA | TCTCAACCTT | CTCTCATCAC | CAACATCATT | AACTGTTTCG | 540 |
| ACCCAGTCCT | CACCTGGCAC | CATGATGCAG | CAGACGCCGT | GCTACTCGTT | TGCGCCACCA | 600 |
| AACACCAGTT | TGAATTCACC | | | | | 620 |

( 2 ) INFORMATION FOR SEQ ID NO:3:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear   ( i i ) MOLECULE TYPE: cDNA   ( x i ) SEQUENCE DESCRIPTION: SEQ ID NO:3:

GCACTGTACA CCAAAGCACG    20

( 2 ) INFORMATION FOR SEQ ID NO:4:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear   ( i i ) MOLECULE TYPE: cDNA   ( x i ) SEQUENCE DESCRIPTION: SEQ ID NO:4:

AACTGTGATC CAGGGCTGTC    20

( 2 ) INFORMATION FOR SEQ ID NO:5:

( i ) SEQUENCE CHARACTERISTICS:
    ( A ) LENGTH: 785 base pairs
    ( B ) TYPE: nucleic acid
    ( C ) STRANDEDNESS: single
    ( D ) TOPOLOGY: linear   ( i i ) MOLECULE TYPE: cDNA   ( i x ) FEATURE:
    ( A ) NAME/KEY: misc_feature
    ( B ) LOCATION: 165..166

( x i ) SEQUENCE DESCRIPTION: SEQ ID NO:5:

| | | | | | |
|---|---|---|---|---|---|
| AGCACTGTAC | ACCAAAGCAC | GATTCCTTCC | AACCCAGACA | GCAGCTCTGC | CTACTGCCTC | 60 |
| CCCAGCACCA | GGCATGGATT | TTCCAGCTAT | ACAGACAGCT | TTGTGCCTCC | GTCGGGGCCC | 120 |
| TCCAACCCCA | TGAACCCCAC | CATTGGCAAT | GGCCTCTCAC | CTCAGAATTC | AATTCGTCAT | 180 |
| AATCTGTCCC | TACACAGCAA | GTTCATTCGT | GTGCAGAATG | AAGGAACTGG | AAAAAGTTCT | 240 |
| TGGTGGATGC | TCAATCCAGA | GGGTGGCAAG | AGCGGGAAAT | CTCCATGGAG | AAGAGCTGCA | 300 |
| TCCATGGACA | ACAACAGTAA | ATTTGCTAAG | AGCCGAAGCC | GAGCTGCCAA | GAAGAAAGCA | 360 |
| TCTCTCCAGT | CTGGCCAGGA | GGGTGCTGGG | GACAGCCCTG | GATCACAGTT | TTCCAAATGG | 420 |
| CCTGCAAGCC | CTGGCTCTCA | CAGCAATGAT | GACTTTGATA | ACTGGAGTAC | ATTTCGCCCT | 480 |
| CGAACTAGCT | CAAATGCTAG | TACTATTAGT | GGGAGACTCT | CACCCATTAT | GACCGAACAG | 540 |
| GATGATCTTG | GAGAAGGGGA | TGTGCATTCT | ATGGTGATCC | CGCCATCTGC | CGCAAAGATG | 600 |

-continued

| | | | | | | |
|---|---|---|---|---|---|---|
| GCCTCTACTT | TACCCAGTCT | GTCTGAGATA | AGCAATCCCG | AAAACATGGA | AAATCTTTTG | 660 |
| GATAATCTCA | ACCTTCTCTC | ATCACCAACA | TCATTAACTG | TTTCGACCCA | GTCCTCACCT | 720 |
| GGCACCATGA | TGCAGCAGAC | GCCGTGCTAC | TCGTTTGCGC | CACCAAACAC | CAGTTTGAAT | 780 |
| TCACC | | | | | | 785 |

We claim:

1. A diagnostic kit for detecting alveolar rhabdomyosarcoma comprising:
   a) a first container comprising a set of PCR primers, wherein a PCR reaction using said set of primers amplifies a DNA molecule from a cDNA generated from mRNA produced by transcription of a chimeric gene generated by a t(2;13) translocation, said set of PCR primers comprising:
      i) a first PCR primer that hybridizes to a nucleotide sequence between nucleotides 9 and 165 of SEQ ID NO:1; and
      ii) a second PCR primer that hybridizes to a nucleotide sequence in SEQ ID NO:2; and,
   b) a second container comprising a DNA molecule equal in size to a DNA molecule that is amplified by PCR using said first PCR primer and said second PCR primer and cDNA generated from a mRNA produced by transcription of a chimeric gene generated by a t(2;13) translocation.

2. A diagnostic kit for detecting alveolar rhabdomyosarcoma comprising:
   a) a first container comprising a set of PCR primers, said set of PCR primers comprising:
      i) a first primer comprising SEQ ID NO:3;
      ii) a second primer comprising SEQ ID NO:4; and,
   b) a second container comprising a DNA molecule of about 410 base pairs.

3. A diagnostic kit for detecting alveolar rhabdomyosarcoma comprising:
   a) a first container comprising a labelled probe; said labelled probe comprising a DNA molecule having a DNA sequence selected from the group consisting of:
      I) a DNA sequence having 100 to 156 contiguous nucleotides identical to a nucleotide sequence between nucleotide 9 and 165 of SEQ ID NO:1; or,
      ii) a DNA sequence having 100 to 156 contiguous nucleotides identical to a nucleotide sequence between nucleotides 198–602 of SEQ ID NO:1; and,
   b) a second container comprising a DNA molecule that comprises an untranslocated PAX3 gene.

4. A diagnostic kit for detecting alveolar rhabdomyosarcoma comprising:
   a set of fluorescent marker-labelled probes; said set of probes comprising:
      a) a first probe comprising a DNA molecule consisting of a nucleotide DNA sequence of 100 to 156 contiguous nucleotides fully complementary or identical to a nucleotide sequence between nucleotides 9 and 165 of SEQ ID NO:1; and,
      b) a second probe comprising a DNA molecule consisting of a nucleotide DNA sequence of between 100 and 500 contiguous nucleotides fully complementary or identical to a nucleotide sequence of SEQ ID NO:2;
   wherein said first probe comprises a fluorescent marker distinguishable from a fluorescent marker label of said second probe.

5. The diagnostic kit of claim 4 wherein:
   a) said first probe comprises SEQ ID NO:3; and
   b) said second probe comprises DNA sequences disclosed in SEQ ID NO:4.

6. A diagnostic kit for detecting alveolar rhabdomyosarcoma comprising:
   a) a first container containing a labelled probe comprising a DNA molecule consisting of a nucleotide DNA sequence of between 100 and 500 nucleotides fully complementary to a nucleotide sequence of SEQ ID NO:5 including nucleotides 165 and 166; and,
   b) a second container containing a DNA molecule that comprises a DNA sequence complementary to said probe.

7. A probe comprising an isolated nucleic acid molecule which consists of a nucleotide DNA sequence of between 100 and 500 nucleotides that is fully complementary to a nucleotide sequence in SEQ ID NO:5 including nucleotides 165 and 166.

8. The isolated probe of claim 1 wherein said nucleic acid molecule is labelled.

9. An isolated nucleic acid molecule consisting of SEQ ID NO:3 or SEQ ID NO:4.

10. The diagnostic kit of claim 3 wherein said probe is labelled with a radioisotope.

11. The diagnostic kit of claim 3 wherein said DNA molecule consists of a nucleotide DNA sequence having 100 and 156 contiguous nucleotides identical to a nucleotide sequence between nucleotides 9 to 165 of SEQ ID NO:1.

12. The diagnostic kit of claim 3 wherein said DNA molecule consists of a nucleotide DNA sequence having 100 to 156 contiguous nucleotides identical to a nucleotide sequence between nucleotides 198 to 602 of SEQ ID NO:1.

13. An isolated nucleic acid molecule consisting of: a DNA sequence identical to nucleotides 9 to 165 of SEQ ID NO:1; or a DNA sequence identical to nucleotides 198 to 602 of SEQ ID NO:1.

14. The isolated nucleic acid molecule of claim 13 consisting of a DNA sequence identical to nucleotides 9 to 165 of SEQ ID NO:1.

15. The isolated nucleic acid molecule of claim 13 consisting of a DNA sequence identical to nucleotides 198 to 602 of SEQ ID NO:1.

16. The isolated nucleic acid molecule of claim 9 consisting of SEQ ID NO:3.

17. The isolated nucleic acid molecule of claim 9 consisting of SEQ ID NO:4.

* * * * *

UNITED STATES PATENT AND TRADEMARK OFFICE
CERTIFICATE OF CORRECTION

PATENT NO. : 5,650,278
DATED : July 22, 1997
INVENTOR(S) : Frederic G. Barr, Beverly S. Emanuel & Naomi Galili It is certified that error appears in the above-indentified patent and that said Letters Patent is hereby corrected as shown below:

In column 1, before BACKGROUND OF THE INVENTION, please make reference to the following Government Grant information:

This work was supported in part by National Institute of Health, grant numbers CA47983 and OM08252. The United States government may have certain rights in this invention.

Signed and Sealed this

Thirteenth Day of October 1998

Attest:

Attesting Officer

BRUCE LEHMAN

*Commissioner of Patents and Trademarks*